United States Patent
Varghese et al.

(10) Patent No.: US 9,239,311 B2
(45) Date of Patent: Jan. 19, 2016

(54) MOLECULARLY IMPRINTED CONDUCTING POLYMER FILM BASED AQUEOUS AMINO ACID SENSORS

(75) Inventors: Saumya Varghese, Thiruvananthapuram (IN); Krishnapillai Padmajakumari Prathish, Thiruvananthapuram (IN); Talasila Prasada Rao, Thiruvananthapuram (IN)

(73) Assignee: Council of Industrial & Scientific Research, New Delhi (IN)

( * ) Notice: Subject to any disclaimer, the term of this patent is extended or adjusted under 35 U.S.C. 154(b) by 259 days.

(21) Appl. No.: 13/983,229

(22) PCT Filed: Jan. 31, 2012

(86) PCT No.: PCT/IN2012/000072
§ 371 (c)(1),
(2), (4) Date: Aug. 1, 2013

(87) PCT Pub. No.: WO2012/104870
PCT Pub. Date: Aug. 9, 2012

(65) Prior Publication Data
US 2013/0306485 A1 Nov. 21, 2013

(30) Foreign Application Priority Data
Feb. 4, 2011 (IN) .............................. 264/DEL/2011

(51) Int. Cl.
*G01N 27/327* (2006.01)
*G01N 33/543* (2006.01)
*G01N 33/68* (2006.01)

(52) U.S. Cl.
CPC .......... *G01N 27/327* (2013.01); *G01N 27/3277* (2013.01); *G01N 33/5438* (2013.01); *G01N 33/6812* (2013.01); *G01N 33/6815* (2013.01); *G01N 2600/00* (2013.01)

(58) Field of Classification Search
CPC ........... C12P 13/12; C12P 13/22; B09C 1/02; C07H 19/044
See application file for complete search history.

(56) References Cited

U.S. PATENT DOCUMENTS

| 4,662,996 A | 5/1987 | Venkatasetty .................. 205/781 |
| 6,743,581 B1 | 6/2004 | Vo-Dinh .......................... 506/39 |

(Continued)

FOREIGN PATENT DOCUMENTS

| CN | 101196486 | 6/2008 |
| EP | 0314009 | 5/1989 |

(Continued)

OTHER PUBLICATIONS

Chen et al., "Selective Determination of Tryptophan by Using a Carbon Paste Electrode Modified with an Overoxidized Polypyrrole Film", *Anal. Sci.* 18:417-421, 2002.

(Continued)

*Primary Examiner* — Jennifer Dieterle
(74) *Attorney, Agent, or Firm* — Norton Rose Fulbright US LLP

(57) ABSTRACT

Molecularly imprinted conducting polymer (MICP) films were electro-polymerized on glassy carbon electrode having specific recognition sites for amino acid viz. L-tyrosine and/or L-cysteine. The amino acid templates in various imprinted films were ejected out by over-oxidation followed by washing and stabilization. Again, the template leached MICP films were modified with metal oxides [oxides of $Cu^{2+}$, $Hg^{2+}$, $Pd^{2+}$, $Au^{3+}$, $Pt^{4+}$ etc]. The resultant template leached MICP and metal oxide modified template leached MICP film based GCE will now selectively sense L-tyrosine and/or L-cysteine in aqueous media by direct and catalytic means respectively employing differential pulse voltammetric waveform. The sensitivity and selectivity of the sensors prepared by the invention are high and the stability is good, which will be widely used in clinical diagnostics, chemical industry, environment protection and other related fields.

14 Claims, 4 Drawing Sheets

(56) References Cited

U.S. PATENT DOCUMENTS

Figure 1:
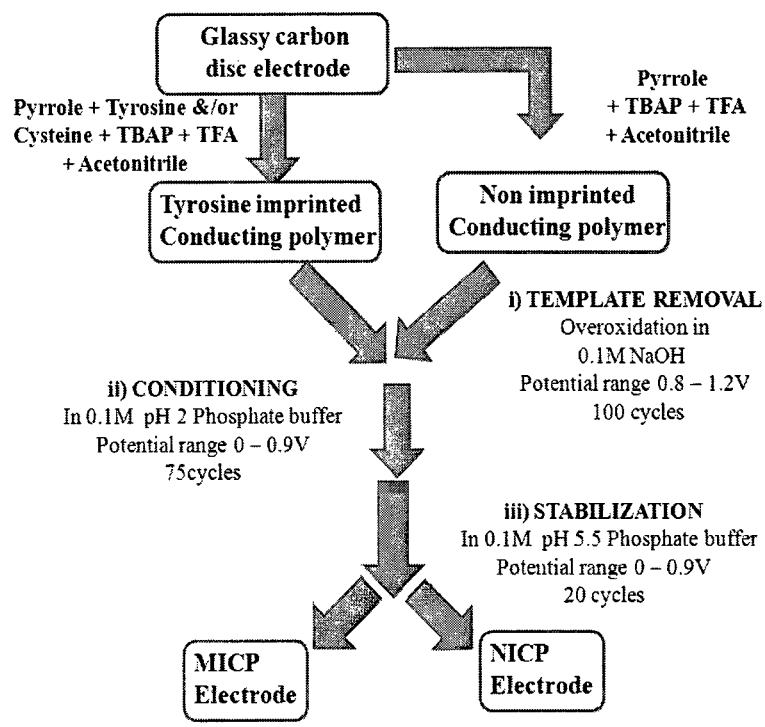

| | | | |
|---|---|---|---|
| 7,598,087 B2 | 10/2009 | Bright | 436/164 |
| 7,741,421 B2 | 6/2010 | Minoura et al. | 526/218.1 |
| 2004/0166581 A1 | 8/2004 | Penelle | 436/2 |
| 2007/0031292 A1 | 2/2007 | Booksh et al. | 422/82.08 |
| 2008/0226503 A1 | 9/2008 | Tai et al. | 422/68.1 |
| 2009/0099301 A1 | 4/2009 | Naraghi et al. | 524/600 |
| 2009/0197297 A1 | 8/2009 | Murray et al. | 435/29 |
| 2009/0318788 A1 | 12/2009 | Levon et al. | 600/345 |
| 2010/0068820 A1 | 3/2010 | Meathrel et al. | 436/95 |
| 2010/0105076 A1 | 4/2010 | Perollier et al. | 435/7.4 |
| 2010/0147683 A1 | 6/2010 | Vanaja et al. | 204/403.01 |

FOREIGN PATENT DOCUMENTS

| | | |
|---|---|---|
| EP | 0658906 | 6/1995 |
| GB | 2337332 | 11/1999 |
| WO | WO 2005/09507 | 2/2005 |
| WO | WO 2007/119229 | 10/2007 |

OTHER PUBLICATIONS

Huang et al., "Sensitive voltammetric determination of tyrosine using multi-walled carbon nanotubes/4-aminobenzeresulfonic acid film-coated glassy carbon electrode", *Collides & Surfaces B. Biointerfaces*, 61(2)176-181, 2008.

International Search Report and Written Opinion issued in PCT application No. PCT/IN2012/000072, mailed Jul. 2, 2012.

Kong et al., "Molecularly imprinted polypyrrole prepared by electrodeposition for the selective recognition of tryptophan enantiomers", *Journal of Applied Polymer Science*, 115(4):1952-1957, 2010.

Li et al., "Electrochemical thin film deposition of polypyrrole on different substrates", *Surface and Coatings Technology*, 198(1-3):474-477, 2005.

Li, "Voltammetric determination of tyrosine based on an L-serine polymer film electrode", *Collides & Surfaces B. Biointerfaces*, 50(2):147-151, 2006.

Liang et al., "Molecularly imprinted electrochemical sensor able to enantroselectivly recognize d and l-tyrosine", *Analytica Chimica Acta*, 542(1):83-89, 2005.

Liu et al., "Improved Voltammetric Response of L-Tyrosine on Multiwalled Carbon Nanotubes-Ionic Liquid Composite Coated Glassy Electrodes in the Presences of Cupric Ion", *Electroanal.*, 20:2148-2152, 2008.

Mazzotta et al., "Development of a sensor prepared by entrapment of MIP particles in electrosynthesised polymer films for electrochemical detection of ephedrine", *Biosensors and Bioelectronics*, 23(7):1152-1156, 2008.

Ozcan et al., "Electrochemical Preparation of a Molecularly Imprinted Polypyrrole-modified Pencil Graphite Electrode for Determination of Ascorbic Acid", *Sensors*, 8:5792-5805, 2008.

Ozkorucuklu et al., "Voltammetric Behaviour of Sulfamethoxazole on Electropolymerized-Molecularly Imprinted Overoxidized Polypyrrole", *Sensors*, 8:8463-8478, 2008.

Pardieu et al., "Molecularly imprinted conducting polymer based electrochemical sensor for detection of atrazine", *Anal. Chim. Acta.*, 649(2):236-245, 2009.

Saumya et al., "In situ copper oxide modified molecularly imprinted polypyrrole film based voltammetric sensor for selective recognition of tyrosine", *Talanta*, 85(2):1056-1062, 2011.

Saumya et al., "Mechanistic aspects of tyrosine sensing on an in situ copper oxide modified molecularly imprinted polypyrrole coated glassy carbon electrode", *Journal of Electroanalytical Chemistry*, 663(2):53-58, 2011.

Song et al., "Dopamine sensor based on molecular imprinted electrosynthesized polymers", *J Solid State Chem.*, 14:1909-1914, 2010.

Syritski et al., "Electrosynthesized molecularly imprinted polypyrrole films for enantioselective recognition of l-aspartic acid", *Electrochimica Acta*, 53(6):2729-2736, 2007.

Tang et al., "Electrochemical determination of L-Tryptophan, L-Tyrosine and L-Cysteine using electrspun carbon nanofibers modified electrode", *Talanta*, 80(5):2182-2186, 2010.

Von Hauff et al., "Biocompatible molecularly imprinted polymers for the voltage regulated uptake and release of l-glutamate in neutral pH solutions", *Biosensors and Bioelectronics*, 26(2):596-601, 2010.

Wang et al., "Determination of tyrosine traces by adsorption voltammetry of its copper (II) complex", *Fresnius J Anal. Chem.*, 351:689-691, 1995.

Xu and Wang, "Electrocatalytic Oxidation and Direct Determination of L-Tyrosine by Square Wave Voltammetry at Multi-Wall Carbon Nanotubes Modified Glassy Carbon Electrodes", *Microchim. Acta*, 151:47-52, 2005.

Zhau et al., "Simultaneous and Direct Determination of Tryptophan and Tyrosine at Boron-Doped Diamond Electrode", *Electroanal.*, 18(8):830-834, 2006.

A

B

MOLECULARLY IMPRINTED CONDUCTING POLYMER FILM BASED AQUEOUS AMINO ACID SENSORS

CROSS-REFERENCE TO RELATED APPLICATIONS

This application is a national phase application under 35 U.S.C. §371 of International Application No. PCT/IN2012/000072 filed 31 Jan. 2012, which claims priority to Indian Application No. 264/DEL/20011 filed 4 Feb. 2011. The entire text of each of the above-referenced disclosures is specifically incorporated herein by reference without disclaimer.

FIELD OF INVENTION

The present invention relates to the process of making "Molecularly imprinted conducting polymer film based aqueous amino acid sensors". The present invention further relates to the process involving coating of glassy carbon electrode (GCE) with molecularly imprinted conducting polymer (more specifically polypyrrole) and metal oxide modified molecularly imprinted conducting polymer films. The present invention particularly relates to a processes involved in modification of GCE with molecularly imprinted polypyrrole and metal oxide modified molecularly imprinted polypyrrole films for selective sensing of particular amino acid(s) (more specifically L-tyrosine and/or L-cysteine) in presence of other amino acids.

BACKGROUND OF THE INVENTION

Zhau et al [Electroanal. 18 (2006)830] have simultaneously determined tyrosine and tryptophan at unmodified boron—doped diamond electrode. Reference is made to several chemically modified electrodes viz. multiwalled carbon nanotube (MWCNT) modified GCE [Microchim. Acta 151 (2005) 47], L-Serine polymer film modified GCE [Colloids & Surfaces B. Biointerfaces 50 (2006)147], and MWCNT-4-aminobenzene sulphonic acid modified GCE [Colloids & surfaces B. Biointerfaces 61 (2008) 176] which are described for tyrosine sensing. Tang et al [Talanta 80 (2010)2182] have reported construction of electrospun carbon nanofibre modified carbon paste electrode for simultaneous voltammetric sensing of L-tyrosine, L-tryptophan and L-cysteine. Reference may be made to Overoxidized polypyrrole modified carbon paste electrode for sensing of tryptophan [Anal. Sci. 18 (2002) 417].

In 2008 Liu et al reported an improved voltammetric response of L-tyrosine employing MWCNT-ionic liquid composite coated GCE in presence of cupric ion [Electroanal. 20 (2008)2148]. Again, two other reports on adsorptive voltammetric determination of tyrosine [Fresnius J. Anal. Chem 351 (1995)689] and enrofloxacin using hanging mercury drop electrode are also described employing copper(II) during voltammetric sensing.

Yet another reference may be made to multifunctional and multispectral biosensor device for polynucleotides, polypeptides & peptides [Vo-Dinh U.S. Pat. No. 6,743,581; 2004], selector molecule adsorbed or immobilized poysiloxane coated biosensor [Levon et. al Inter. Pat. No. WO 059507; 2005], chemical sensor featuring dual sensing (surface plasmon resonance & fluorescence detection) motif for sensing pinacolyl methyl phosphonate [Booksh et al, U.S. Pat. No. 0,031,292; 2007]. References may be made to a method for a conducting polymer coated sensing electrode for detecting polar toxic species [Venkatasetty, U.S. Pat. No. 4,662,996; 1987], protein adsorbed shapable electroconductive polymer film[Wolfgang et al, Euro. Pat. No. 0658906; 1994], sensor comprising a substrate containing nanoparticles of a conducting polymer, polyaniline[Morrin et al, Int. Pub. No. WO2007/119229; 2007], a method of determining analyte concentrations by utilizing analyte sensors that employ conducting organic polymers covalently functionalized with an enzyme, antigen or an ion specific binding site and employed in a diagnostic device to selectively assay a liquid medium [Albarella et al, Euro. Pub. No. 0314009; 1988]. The drawbacks of the above mentioned matrices for sensing amino acids are the lack of selectivity, poor stability, need to incorporate selective recognition moieties in the conducting polymer or other matrices like MWCNT, L-serine etc. Another reference may be made to a few molecularly imprinted electrosynthesized polymer modified electrodes viz. copolymerization of o-phenylenediamine and resorcinol for sensing of dopamine [J. Solid state chem. 14 (2010)1909], polypyrrole for ascorbic acid sensing [Sensors 8 (2008)5792], overoxidised polypyrrole for sulphamethaxozole sensing [Sensors 8 (2008)8463] and molecularly imprinted poly (3,4-ethylene dioxythiophene-co-thiophene acetic acid] employing platinum electrode for atrazine sensing [Anal. Chim Acta 649 (2009) 236].

Yet another reference may be made to imprinted polymer based quartz crystal microbalance sensors using polymerizable chiral derivatives of cysteine and homocysteine for peptide templates like Oxytocin, Vasopressin, Angiotensin II, Bradykinin and 15-mer peptide [Tai et al U.S. Pat. No. 0,226,503; 2008], dual MIP/QCM sensor for polychloroaromatic contaminants [Penelle, U.S. Pat. No. 0,166,581; 2004], analysis kit for sensing dopamine & ochratoxin A [Perollier et al U.S. Pat. No. 0,105,076; 2010], affinity electrode modified with synthetic polymers for the detection of phenols, morphines and phenoxy acid herbicides [Kroger & Mosbach GB Pat. No. 2337332; 1999], process for fabrication of ISFET based potentiometric sensor coated with molecular imprint of cholesterol [Vanaja et al, U.S. Pat. No. 0,147,683; 2010], molecularly imprinted sensor device for detecting drugs like gamma hydroxy butyrate (GHB), ketamine and cortisol [Murray et al U.S. Pat. No. 0,197,297; 2009], bionic nanosensing film of electrochemical transducer [Zhou et al Chinese Pat. No. CN 101196486; 2008], method for producing macromolecule identifying polymer [Minoura et al, U.S. Pat. No. 7,741,421; 2010], peptide imprinted polymers with integrated emission sites (PIPIES) [Bright, U.S. Pat. No. 7,598,087; 2009], method of combining surface molecular imprinting (SMI) with the production of self-assembled monolayers (SAM) on gold coated chip surfaces for the detection of cancer biomarkers [Levon et al U.S. Pat. No. 0,318,788; 2009] and a method of molecular imprinting for recognition in aqueous media [Naraghi et al U.S. Pat. No. 0,099,301; 2009]. MIPs are formulated as an adhesive in an in-vitro diagnostic device to release template molecules to capture target molecules [Meathrel et al U.S. Pat. No. 0,068,820; 2010].

The above mentioned references pertaining to molecular imprinted substrates are superior to other sensing platforms due to excellent predetermined selectivity, ruggedness, can afford absence of specific reagents for selective molecular recognition as the cavities inside the polymer matrices itself are tailor made for the analyte under consideration rendering a label free sensing. However, the present embodiment holds an extra advantage which synchronizes the high selectivity of imprinted polymers with the excellent conducting properties of conducting polymers viz. polypyrrole which improves the signal transduction considerably. Also, the enhanced catalytic properties rendered by metal oxide makes the present embodiment an excellent sensing platform with good sensitivities and remarkable selectivity.

OBJECTIVES OF THE INVENTION

The main object of the present invention is to provide "Molecularly imprinted conducting polymer film based aqueous amino acid sensors" which obviates the drawbacks mentioned above.

Another object of the present invention is to prepare molecularly imprinted conducting polymer (MICP) film on GCE surface.

Yet another object of the present invention is to form metal oxide modified MICP film in presence of $Cu^{2+}$, $Hg^{2+}$, $Pd^{2+}$, $Au^{3+}$ & $Pt^{4+}$ onto GCE surface.

Still another object of the present invention is to construct L-tyrosine and/or L-cysteine sensor for their monitoring in aqueous media in presence of other amino acids.

Still yet another object of present invention is reusability and regenerability of MICP and metal oxide modified MICP film coated GCE surface.

SUMMARY OF THE INVENTION

Accordingly, the present invention relates to an amino acid sensor comprising a substrate coated with a polymer selected from molecularly imprinted conducting polymer (MICP) or metal oxide modified molecularly imprinted conducting polymer (MOMICP).

In one embodiment of the invention, the substrate is a glassy carbon electrode (GCE) surface.

In another embodiment of the invention, amino acid used for imprinting the polymer is selected from the group consisting of L-tyrosine, L-cysteine and a combination thereof.

In yet another embodiment of the invention, said sensor selectively senses amino acids in aqueous solutions.

Yet another embodiment of the invention provides a process of preparing amino acid sensor comprising a substrate coated with a polymer selected from molecularly imprinted conducting polymer (MICP) or metal oxide modified molecularly imprinted conducting polymer (MOMICP), comprising the steps of:
(a) electropolymerizing pyrrole monomer in the presence of template of amino acid selected from the group consisting of L-tyrosine, L-cysteine and a combination thereof to be imprinted in acetonitrile containing tetrabutyl ammonium perchlorate and trifluoacetic acid onto a substrate to obtain molecularly imprinted conducting polymer film based electrode;
(b) leaching out the template from the electrode as obtained in step (a) by electrochemical over-oxidation followed by washing by cycling in phosphate buffer of pH 2 and subsequently stabilizing in phosphate buffer of pH 5.5 to obtain the template leached MICP, or dual template leached MICP film coated electrode;
(c) depositing metal selected from a group consisting of $Cu^{2+}$, $Hg^{2+}$, $Pd^{2+}$, $Au^{3+}$, $Pt^{4+}$ on to the template leached and stabilized MICP or dual template leached MICP electrode as obtained in step (b) followed by anodically scanning to obtain respective metal oxide modified molecularly imprinted conducting polymer film coated electrode to be used as amino acid sensor.

In yet another embodiment of the invention, the ratio of pyrrole and the template used in the process as claimed in claim 5 is maintained between 400:1 to 2:1 within the concentration ranges of $2\times10^{-3}$ to $4\times10^{-3}$ M of pyrrole and $10^{-5}$ to $10^{-3}$ M of the template. In yet another embodiment of the invention, in step (a) volume of the acetonitrile is 20 ml, volume of the trifluoacetic acid is in the range of 0.5 to 35 μl and concentration of the tetrabutyl ammonium perchlorate is in the range of 0.01 to 0.1M.

In yet another embodiment of the invention, in step (a) electropolymerization is done at a deposition potential ranging from 0.8 to 0.9V vs Ag/AgCl for a period in the range of 55 to 65 s.

In yet another embodiment of the invention, in step (a) the substrate is a glassy carbon electrode (GCE) surface.

In yet another embodiment of the invention, in step (b) the electrochemical over-oxidation is done in the presence of 0.08-0.1M NaOH at a potential ranging between 0.8 to 1.2V vs Ag/AgCl for a minimum of 100 times at a scan rate of 40-70 mV/s.

In yet another embodiment of the invention, in step (b) washing is done by cycling in phosphate buffer for a minimum of 75 times in the potential ranging between 0 to 0.9V vs Ag/AgCl at a scan rate in the range of 75 to 125 mV/s.

In yet another embodiment of the invention, in step (b) stabilizing is done at a potential ranging between 0-0.9 V for a minimum of 20 times at a scan rate in the range of 50 to 70 mV/s.

In yet another embodiment of the invention, in step (c) the deposition of metals on the electrode obtained in step (b) is done by holding the electrode potentiostatically in the range of −0.28 to −0.32V for a period ranging between 4.5 to 5 seconds.

In yet another embodiment of the invention, in step (c) anodic scanning is done at a potential in the range of 0 to 0.9V.

In yet another embodiment of the invention, the coated electrode of step (b) or (c) is reusable for 25 to 35 times by bringing back to starting potential in the range of −0.15 to 0.075 V and stirring in pH 5.5 phosphate buffer.

In yet another embodiment of the invention, the coated electrodes of step (b) or (c) can be regenerated after use by holding the electrodes at a potential in the range of −0.15 to 0.075V for a period in the range of 7 to 10 seconds for metal oxide removal, in case of metal oxide modified MICP, followed by stirring in pH 5.5 phosphate buffer for all modified electrodes for a period in the range of 1 to 5 min to remove oxidized tyrosine.

In yet another embodiment of the invention, said process further comprises a step of calibration of the amino acid sensor by dipping the coated electrode obtained in steps (b) or (c) of claim 5 as working electrode, platinum foil counter electrode and Ag/AgCl reference electrode in an electrochemical cell containing known amount of amino acid in 0.075 to 0.15 M phosphate buffer solution followed by recording of differential pulse voltammograms by scanning in a potential ranging between 0 to 0.9V at modulation amplitude in the range of 50 to 300 mV to prepare a calibration graph by plotting current flowing between working and counter electrodes against amino acid concentration.

Still another embodiment of the invention provides a method of selectively sensing amino acids by using amino acid sensor, comprising the steps of:
i) installing the coated electrode as obtained in steps (b) or (c) of claim 5 as amino acid sensor in an electrochemical cell which contains sample to be analyzed at a pH ranging between 5.5 to 7.0 followed by recording of differential pulse voltammograms by scanning in the potential ranging between 0 to 0.9V at modulation amplitude in the range of 50 to 300 mV;
(ii) determining unknown concentration of amino acids by referring to a calibration graph.

BRIEF DESCRIPTION OF ACCOMPANYING DRAWINGS

FIG. 1 Process for preparation of molecularly imprinted conducting polymer (MICP) & non-imprinted CP (NICP) films on to GCE.

Figure 2:
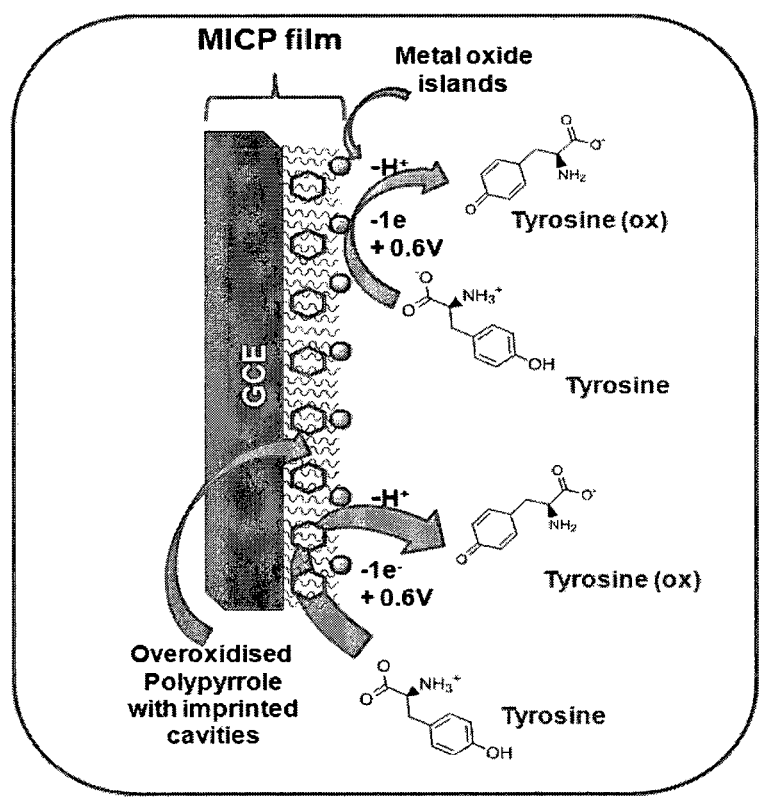

FIG. 2 Schematic diagram of metal oxide modified MICP based amino acid sensor.

Figure 3:
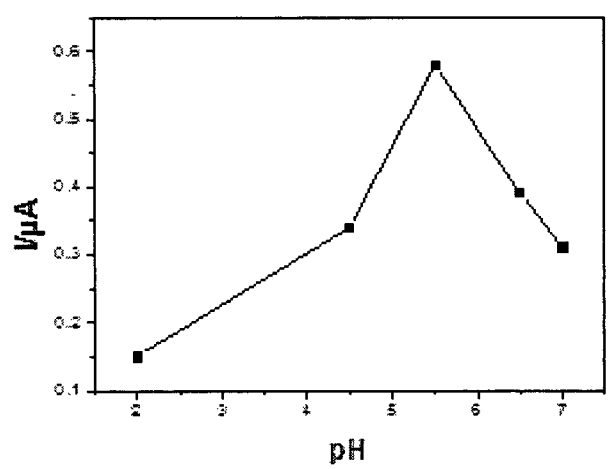

FIG. 3 Effect of pH on L-tyrosine response with metal oxide (specifically copper oxide) modified MICP (specifically MI polypyrrole) film based sensor.

Figure 4:
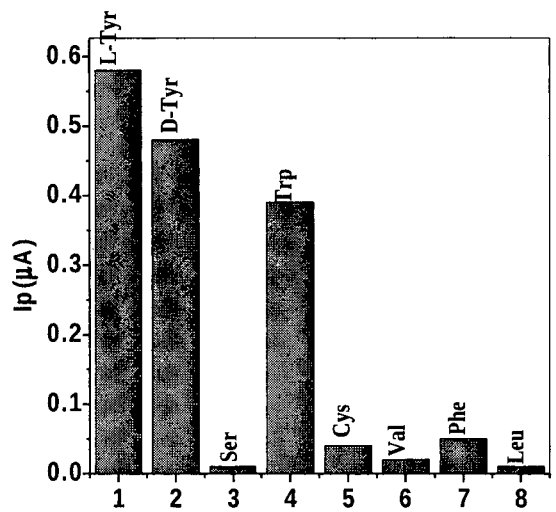
Figure 4:
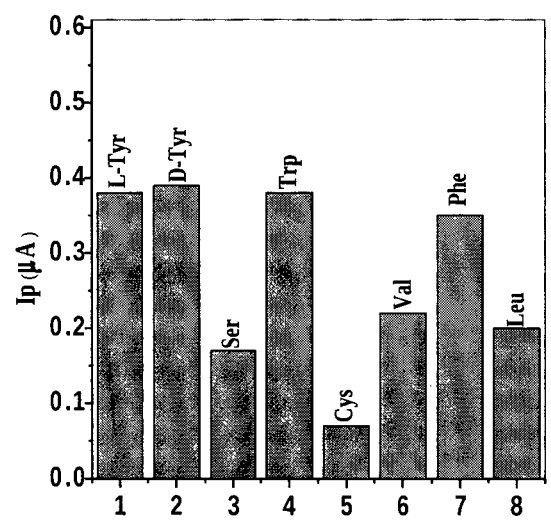

FIG. 4 Voltammetric sensing signals for molecularly imprinted (A) and corresponding non imprinted (B) metal oxide (specifically copper oxide) modified polypyrrole films with various amino acids.

DETAILED DESCRIPTION OF THE INVENTION

The present invention provides "molecularly imprinted conducting polymer film based aqueous amino acid sensors" which comprises
- a process of construction of modified electrodes for sensing of amino acids employing molecular imprinted conducting polymer (MICP) on suitable substrate preferably glassy carbon disc or electrode;
- over-oxidation, washing and stabilization of MICP;
- modification of template leached MICP with metal oxide [by electrodeposition of metal from $Cu^{2+}$, $Hg^{2+}$, $Pd^{2+}$, $Au^{3+}$, $Pt^{4+}$ etc. solutions] and anodic oxidation;
- selective sensing of L-tyrosine and/or L-cysteine in presence of other amino acids.

The present invention offers a process for making amino acid sensing films having specific, accessible and homogenous imprinted sites. The above mentioned amino acid sensing films when coated on indicator electrode in form of disc selectively senses targeted amino acid in aqueous media after ejecting out the template amino acid by over-oxidation, washing and stabilization steps. NICPs prepared in the absence of template(s) exhibit sensing due to the surface adsorption of the analytes unlike MICPs, where the analyte rebinding into the imprinted cavities trigger the sensing. However, NICPs lack selectivity due to non specific binding of analytes. The salient features of the invention include the following
- A process of making MICP and metal oxide modified MICP film coated GCE are described. The electrocatalytic effect of the metal oxides generates an amplified analytical signal in the case of MOMICP over and above the selectivity provided by MICPs.
- Pretreatment (overoxidation, washing and stabilization) of the film is carried out in case of MICP (to eject the template molecule)
- Selective sensing of targeted amino acid in aqueous media is described.

Process of Making Tailored Amino Acid Sensing Films

The preparation of tailored molecularly imprinted conducting polymer (MICP) films on glassy carbon electrode involves:

i) electropolymerisation of pyrrole monomer in acetonitrile medium containing 0.01 M tetrabutyl ammonium perchlorate in presence of template: L-tyrosine and/or L-cysteine (in presence of tri-fluoro acetic acid to aid dissolution of template). FIGS. 1 & 2 depicts flow chart and schematic diagram of the process of making of MICP film based L-tyrosine and/or L-cysteine sensor. Non-imprinted conducting polymer (NICP) films were analogously prepared by following the above mentioned procedure but omitting the template molecule.

Metal oxide modified MICP films were prepared by subjecting amino acid template leached MICP films in pH 5.5 phosphate buffer media for 5 s at −0.30V in presence of respective metal ions $Cu^{2+}$, $Hg^{2+}$, $Pd^{2+}$, $Au^{3+}$, $Pt^{4+}$ etc. and scanning anodically (See FIG. 2). Incorporation of metal ions can enhance the analytical signal in view of the electrocatalytic properties exhibited by certain metal ion/oxides. The electrocatalysis of metal oxide islands as well as the metal-amino acid complex formation is responsible for enhanced oxidation of L-tyrosine at the electrode—solution interface as shown in FIG. 2 resulting in an amplified anodic peak current.

ii) Pretreatment of the Film

FIG. 1 highlights the detailed steps involved in pretreatment of MICP and NICP films in form of flow chart. MICP and NICP films were subjected to potentiodynamic electrochemical overoxidation at 0.8-1.2V for 100 cycles in 0.1M NaOH solution to eject the template(s). Then the films were washed in weakly acidic phosphate buffer by repeated cycling in the potential range 0 to 0.9V for 75 cycles and then stabilized in pH 5.5 phosphate medium by repeated cycling in the potential range 0 to 0.9V for 20 cycles to obtain leached films.

iii) Selective Sensing

The process of making amino acid (L-tyrosine and/or L-cysteine) sensor is shown schematically in FIGS. 1 & 2. The resulting sensor distinguishes analyte amino acid, from other amino acids. The effect of pH on sensing signal of amino acid (more specifically L-tyrosine) sensor is shown in FIG. 3.

Determination of L-Tyrosine and/or L-Cysteine

Appropriate amounts of L-tyrosine and/or L-cysteine ($1 \times 10^{-8}$ to $8 \times 10^{-6}$M) in 0.1M phosphate buffer solution (pH 5.5) were taken in 20 ml electrochemical cell, and then 3 electrode system was installed on it where in the working electrodes are NICP, MICP and MOMICP film coated electrodes. Differential pulse voltammograms were recorded by scanning in the potential window 0 to 0.9V at modulation amplitude of 100 mV. The unknown concentrations of L-tyrosine and/or L-cysteine were determined by referring to the calibration graph.

Selectivity Studies Using Copper Oxide Modified MICP and NICP Films

Detailed selectivity studies were undertaken with copper oxide modified MICP and corresponding NICP coated GCE for L-tyrosine and other amino acids. The results obtained are shown in FIGS. 4A & 4B respectively. The selectivity factors for L-tyrosine in admixtures show about 50-60 fold selectivities for L-tyrosine over serine, cysteine, valine, phenylalanine and leucine, 1.2 fold over D-Tyrosine and 1.5 fold for tryptophan respectively. Molecular imprinting resulted in better selectivity factors with both individual and in admixtures (mainly undertaken to simulate real sample solution) showing significant imprinting effect.

Analysis of Synthetic Samples

Table 1 shows the results obtained on analysis of synthetic human urine samples. The simulated synthetic urine sample was prepared by mixing $8 \times 10^{-7}$M Serine, $8 \times 10^{-7}$ M Alanine, $4 \times 10^{-7}$M Valine, $4 \times 10^{-7}$M Phenylalanine and $4 \times 10^{-7}$M Leucine respectively in the proportion corresponding to human urine sample. Appropriate amounts of L-tyrosine ($1 \times 10^{-7}$ to $4 \times 10^{-6}$M) in 0.1M phosphate buffer solution (pH 5.5) containing the above synthetic sample were taken in 20 ml electrochemical cell, and then 3 electrode system consisting of MOMICP as working electrode and platinum foil & Ag/AgCl as counter and reference electrodes respectively was installed on it. Differential pulse voltammograms were recorded by scanning in the potential window 0 to 0.9V at modulation amplitude of 100 mV. The unknown concentration of L-tyrosine was determined by referring to the calibration graph drawn between current passed between working and platinum foil counter electrode at peak potential of L-tyrosine. Quantitative recoveries of spiked samples were obtained as shown in Table 1.

TABLE 1

Analysis of Synthetic human urine samples*

| Sl. No. | L-tyrosine Added(M) | L-tyrosine found(M)* | Recovery (%) |
|---|---|---|---|
| 1 | $1 \times 10^{-7}$ | $1.06 \times 10^{-7}$ | 106.0 |
| 2 | $2 \times 10^{-6}$ | $1.95 \times 10^{-6}$ | 97.5 |
| 3 | $3 \times 10^{-6}$ | $3.09 \times 10^{-6}$ | 103.0 |
| 4 | $4 \times 10^{-6}$ | $3.96 \times 10^{-6}$ | 97.5 |

*$8 \times 10^{-7}$ M Serine + $8 \times 10^{-7}$ M Alanine + $4 \times 10^{-7}$ M Valine + $4 \times 10^{-7}$ M Phenylalanine + $4 \times 10^{-7}$ M Leucine Analysis of Urine Samples The applicability of the developed sensing strategy for analyzing L-tyrosine in human urine sample was carried out. Appropriate amounts of L-tyrosine ($1 \times 10^{-6}$ and $2 \times 10^{-6}$M) in 0.1M phosphate buffer solution (pH 5.5) in presence of urine samples were taken in 20 ml electrochemical cell, and then 3 electrode system consisting of MOMICP as working electrode and platinum foil & Ag/AgCl as counter and reference electrodes respectively was installed on it. Differential pulse voltammograms were recorded by scanning in the potential window 0 to 0.9V at modulation amplitude of 100 mV. The unknown concentrations of L-tyrosine were determined by referring to the calibration graph drawn between current passed between working and platinum foil counter electrodes at peak potential of L-tyrosine (See Table 2). Table 2 also shows quantitative recoveries upon spiking known amounts of tyrosine to human urine samples.

TABLE 2

Analysis of Human urine samples

| Sl. no. | Sample | L-tyrosine Added (M) | L-tyrosine found (M)* | Recovery (%) |
|---|---|---|---|---|
| 1 | Human urine | — | $3.3 \times 10^{-7}$ | — |
| 2 | Human urine | $1 \times 10^{-6}$ | $1 \times 10^{-6}$ | $103.0 \pm 6$ |
| 3 | Human urine | $2 \times 10^{-6}$ | $2.1 \times 10^{-6}$ | $99.6 \pm 3.1\%$ |

*average of three determinations

Having described the invention, the following examples are given to illustrate the process of making of molecularly imprinted conducting polymer (MICP), non imprinted conducting polymer (NICP) and metal oxide modified MICP films.

EXAMPLES

The following examples are given by way of illustrations and should not be construed so as to limit the scope of the invention.

Method of Preparation of MICP Film for Sensing L-Tyrosine

Example 1

The MICP film was prepared by electropolymerising 0.002M (0.134 µg/ml) of pyrrole in 20 ml of acetonitrile as supporting electrolyte containing 0.01M of tetrabutyl ammonium perchlorate and 35 µl trifluoroacetic acid at a deposition potential of 0.9V vs Ag/AgCl for a duration of 60 s in presence of $10^{-3}$M of L-tyrosine template onto glassy carbon electrode. The electrode was then taken out and template is then ejected out by electrochemical overoxidation in sodium hydroxide (>0.1M) by repeated cycling in the potential window of 0.8 to 1.2V vs Ag/AgCl for a minimum of 100 times at scan rate of 50 mV/s. The template leached MICP film electrode is then washed by cycling a minimum of 75 times in the potential window of 0 to 0.9V vs Ag/AgCl at scan rate of 100 mV/s. Subsequently, the above film electrode is stabilized in pH 5.5 phosphate buffer by cycling in the potential window of 0 to 0.9V for minimum of 20 times at 50 mV/s to obtain MICP film based electrode for L-tyrosine sensing.

Example 2

The MICP film was prepared by electropolymerising 0.003M (0.201 µg/ml) of pyrrole in 20 ml of acetonitrile as supporting electrolyte containing 0.01M of tetrabutyl ammonium perchlorate and 35 µl of trifluoroacetic acid at a deposition potential 0.9 V vs Ag/AgCl for a duration of 60 s in presence of $10^{-3}$M of L-tyrosine or L-cysteine or combination of L-tyrosine and L-cysteine template(s) onto glassy carbon electrode. The electrode was then taken out and template is then ejected out by electrochemical over oxidation in sodium hydroxide (>0.1M) by repeated cycling in the potential window of 0.8 to 1.2V vs Ag/AgCl for a minimum of 100 times at scan rate of 50 mV/s. The template leached MICP film electrode is then washed by cycling a minimum of 75 times in the potential window of 0 to 0.9V vs Ag/AgCl at scan rate of 100 mV/s. Subsequently, the above film electrode is stabilized in pH 5.5 phosphate buffer by cycling in the potential window of 0 to 0.9V for minimum of 20 times at 50 mV/s to obtain MICP film based electrode for L-tyrosine, L-cysteine and combination of L-tyrosine & L-cysteine sensing.

Example 3

The MICP film was prepared by electropolymerising 0.004M (0.268 µg/ml) of pyrrole in 20 ml of acetonitrile as supporting electrolyte containing 0.01M of tetrabutyl ammonium perchlorate and 35 µl of trifluoroacetic acid at a deposition potential 0.9V vs Ag/AgCl for a duration of 60 s in presence of $10^{-3}$M of L-tyrosine template onto glassy carbon electrode. The electrode was then taken out and template is then ejected out by electrochemical overoxidation in sodium hydroxide (>0.1M) by repeated cycling in the potential window of 0.8 to 1.2V vs Ag/AgCl for a minimum of 100 times at scan rate of 50 mV/s. The template leached MICP film electrode is then washed by cycling a minimum of 75 times in the potential window of 0 to 0.9V vs Ag/AgCl at scan rate of 100 mV/s. Subsequently, the above film electrode is stabilized in pH 5.5 phosphate buffer by cycling in the potential window of 0 to 0.9V for minimum of 20 times at 50 mV/s to obtain MICP film based electrode for L-tyrosine sensing.

Example 4

The MICP films were prepared by electropolymerisation as in examples 1, 2 and 3 using 0.1 M tetrabutyl ammonium perchlorate in 20 ml acetonitrile Example 5

The MICP films were prepared as in examples 1, 2, 3 and 4 with 0.8V as deposition potential during electropolymerisation.

Example 6

The MICP films were prepared as in examples 1, 2, 3, 4 and 5 using 65 seconds as the duration time for electropolymerisation.

Example 7

The MICP films were prepared as in example 1, 2, 3, 4, 5 and 6 using 55 seconds as the duration time for electropolymerisation.

Example 8

The MICP films were prepared as in examples 1, 2, 3, 4, 5, 6 and 7 using 0.5 µl of trifluoroacetic acid and $10^{-5}$M L-tyrosine as the template.

Method of Preparation of Non Imprinted Conducting Polymer (NICP) Film

Example 9

The NICP film was prepared by electropolymerizing 0.002M (0.134 µg/ml) of pyrrole in 20 ml of acetonitrile as supporting electrolyte containing 0.01M of tetrabutyl ammonium perchlorate and 35 µl of trifluoroacetic acid at a deposition potential of 0.9 V vs Ag/AgCl for a duration of 60 s. The electrode was then subjected to electrochemical overoxidation in 0.1M sodium hydroxide by repeated cycling in the potential window 0.8 to 1.2V vs Ag/AgCl for a minimum of 100 times at a scan rate of 50 mV/s. The NICP film electrode is then washed by cycling a minimum of 75 times in the potential window of 0 to 0.9V vs Ag/AgCl at a scan rate of 100 mV/s. Subsequently, the above film electrode was then stabilized in pH 5.5 phosphate buffer by cycling in the potential window of 0 to 0.9V for a minimum of 20 times at 50 mV/s to obtain NICP film based electrode for L-tyrosine and/or L-cysteine sensing.

Method of Preparation of Metal Oxide Modified MICP (MO-MICP) Film for L-Tyrosine Sensing

Example 10

Metal oxide modified MICP film was prepared by potentiostatic deposition of metals on to template leached MICP film from $3\times10^{-5}$M of $Cu^{2+}$ or $Hg^{2+}$ or $Pd^{2+}$ or $Au^{2+}$ or $Pt^{4+}$ etc solutions for 5 s at −0.3V and then anodically scanning in the potential window of 0 to 0.9V to form corresponding metal oxide coatings for selective sensing of L-tyrosine.

Example 11

Metal oxide modified MICP film was prepared by potentiostatic deposition of metals on to template leached MICP film from $1\times10^{-4}$M of $Cu^{2+}$ or $Hg^{2+}$ or $Pd^{2+}$ or $Au^{3+}$ or $Pt^{4+}$ etc solutions for 5 s at −0.3V and then anodically scanning in the potential window of 0 to 0.9V to form corresponding metal oxide coatings for selective sensing of L-tyrosine.

Example 12

Metal oxide modified MICP film was prepared by potentiostatic deposition as in example 10 and 11 for duration of 5 s at −0.28V.

Example 13

Metal oxide modified MICP film was prepared by potentiostatic deposition as in example 10 and 11 for duration of 5 s at −0.32V.

Example 14

Metal oxide modified MICP film was prepared by potentiostatic deposition as in example 10 and 11 for duration of 4 s at −0.3V.

Example 15

Metal oxide modified MICP film was prepared by potentiostatic deposition as in example 10 and 11 for duration of 4 s at −0.28V.

Example 16

Metal oxide modified MICP film was prepared by potentiostatic deposition as in example 10 and 11 for duration of 4 s at −0.32V.

Method of Preparation of Metal Oxide Modified MICP (MO-MICP) Film for L-Cysteine Sensing

Example 17

Metal oxide modified MICP film was prepared by potentiostatic deposition of $3\times10^{-5}$M of $Cu^{2+}$ solution on to template leached MICP film for 5 s at −0.3V and then anodically scanning in the potential window of 0 to 0.9V to form corresponding metal oxide coatings for selective sensing of L-cysteine.

Example 18

Metal oxide modified MICP film was prepared by potentiostatic deposition from $1\times10^{-4}$M of $Cu^{2+}$ solution on to template leached MICP film for 5 s at −0.3V and then anodically scanning in the potential window of 0 to 0.9V to form corresponding metal oxide coatings for selective sensing of L-cysteine.

Example 19

Metal oxide modified MICP film was prepared by potentiostatic deposition as in example 17 and 18 for duration of 5 s at −0.28V.

Example 20

Metal oxide modified MICP film was prepared by potentiostatic deposition as in example 17 and 18 for duration of 5 s at −0.32V.

Example 21

Metal oxide modified MICP film was prepared by potentiostatic deposition as in example 17 and 18 for duration of 4 s at −0.3V.

Example 22

Metal oxide modified MICP film was prepared by potentiostatic deposition as in example 17 and 18 for duration of 4 s at −0.28V.

Example 23

Metal oxide modified MICP film was prepared by potentiostatic deposition as in example 17 and 18 for duration of 4 s at −0.32V.

Method of Preparation of Metal Oxide Modified MICP (MO-MICP) Film for L-Tyrosine and L-Cysteine Sensing

Example 24

Metal oxide modified MICP film was prepared by potentiostatic deposition from $3\times10^{-5}$M of $Cu^{2+}$ solution on to template leached MICP film for 5 s at −0.3V and then anodically scanning in the potential window of 0 to 0.9V to form corresponding metal oxide coatings for selective sensing of L-tyrosine and L-cysteine.

Example 25

Metal oxide modified MICP film was prepared by potentiostatic deposition from $1\times10^{-4}$M of $Cu^{2+}$ solution on to template leached MICP film for 5 s at −0.3V and then anodically scanning in the potential window of 0 to 0.9V to form corresponding metal oxide coatings for selective sensing of L-tyrosine and L-cysteine.

Example 26

Metal oxide modified MICP film was prepared by potentiostatic deposition as in example 24 and 25 for duration of 5 s at −0.28V.

Example 27

Metal oxide modified MICP film was prepared by potentiostatic deposition as in example 24 and 25 for duration of 5 s at −0.32V.

Example 28

Metal oxide modified MICP film was prepared by potentiostatic deposition as in example 24 and 25 for duration of 4 s at −0.3V.

Example 29

Metal oxide modified MICP film was prepared by potentiostatic deposition as in example 24 and 25 for duration of 4 s at −0.28V.

Example 30

Metal oxide modified MICP film was prepared by potentiostatic deposition as in example 24 and 25 for duration of 4 s at −0.32V.

Experimental Procedure for the Determination of L-Tyrosine Using MOMICP Modified Electrode.

Example 31

Appropriate amounts of L-tyrosine ($1\times10^{-8}$ to $8\times10^{-6}$M) in 0.1M phosphate buffer solution (pH 5.5) were taken in 20 ml electrochemical cell, and then 3 electrode system was installed on it where in the working electrode is copper oxide modified MICP film coated glassy carbon electrodes and Platinum(Pt) foil and Ag/AgCl are counter and reference electrodes respectively. Differential pulse voltammograms were recorded by scanning in the potential window of 0 to 0.9V at modulation amplitude of 100 mV. The unknown concentrations of L-tyrosine was determined by referring to the calibration graph.

TABLE 3

Calibration Graph for determining concentration of L-Tyrosine

| Sl no. | Tyrosine Concentration(M) | Ip(μA) |
| --- | --- | --- |
| 1 | $10^{-8}$ | 0.11 |
| 2 | $5 \times 10^{-8}$ | 0.23 |
| 3 | $10^{-7}$ | 0.31 |
| 4 | $5 \times 10^{-7}$ | 0.49 |
| 5 | $10^{-6}$ | 0.59 |
| 6 | $2 \times 10^{-6}$ | 0.79 |
| 7 | $3 \times 10^{-6}$ | 0.97 |
| 8 | $4 \times 10^{-6}$ | 1.09 |
| 9 | $5 \times 10^{-6}$ | 1.26 |
| 10 | $6 \times 10^{-6}$ | 1.4 |
| 11 | $7 \times 10^{-6}$ | 1.62 |
| 12 | $8 \times 10^{-6}$ | 1.81 |

Experimental Procedure for the Determination of L-Cysteine Using MOMICP Modified Electrode.

Example 32

Appropriate amounts of L-cysteine ($1\times10^{-8}$ to $8\times10^{-6}$M) in 0.1M phosphate buffer solution (pH 5.5) were taken in 20 ml electrochemical cell, and then 3 electrode system was installed on it where in the working electrode is copper oxide modified MICP film coated glassy carbon electrode and Pt foil and Ag/AgCl are counter and reference electrodes respectively. Differential pulse voltammograms were recorded by scanning in the potential window of 0 to 0.9V at modulation amplitude of 100 mV. The unknown concentrations of L-cysteine was determined by referring to the calibration graph.

TABLE 4

Calibration Graph for determining concentration of L-cysteine

| Sl no. | Cysteine Concentration(M) | Ip(μA) |
| --- | --- | --- |
| 1 | $10^{-8}$ | 0.17 |
| 2 | $5 \times 10^{-8}$ | 0.38 |
| 3 | $10^{-7}$ | 0.59 |
| 4 | $5 \times 10^{-7}$ | 0.87 |
| 5 | $10^{-6}$ | 1.09 |
| 6 | $2 \times 10^{-6}$ | 1.39 |
| 7 | $3 \times 10^{-6}$ | 1.61 |
| 8 | $4 \times 10^{-6}$ | 1.78 |
| 9 | $5 \times 10^{-6}$ | 1.99 |
| 10 | $6 \times 10^{-6}$ | 2.11 |
| 11 | $7 \times 10^{-6}$ | 2.31 |
| 12 | $8 \times 10^{-6}$ | 2.44 |

Experimental Procedure for the Determination of Dual Template (L-Tyrosine and L-Cysteine) Using MOMICP Modified Electrode

Example 33

Appropriate amounts of L-tyrosine and L-cysteine ($1\times10^{-8}$ to $8\times10^{-6}$M) in 0.1M phosphate buffer solution (pH 5.5) were taken in 20 ml electrochemical cell, and then 3 electrode system was installed on it where in the working electrode is copper oxide modified MICP film coated glassy carbon electrode and Pt foil and Ag/AgCl are counter and reference electrodes respectively. Differential pulse voltammograms were recorded by scanning in the potential window of 0 to 0.9V at modulation amplitude of 100 mV. The unknown concentrations of L-tyrosine and L-cysteine were determined by referring to the calibration graph.

TABLE 5

Calibration Graph for determining concentrations of L-tyrosine and L-cysteine

| Sl. no | L-Cysteine & L-Tyrosine Concentration(M) | $Ip(\mu A)$ L-Cysteine | L-Tyrosine |
|---|---|---|---|
| 1 | $10^{-8}$ | 0.15 | 0.10 |
| 2 | $5 \times 10^{-8}$ | 0.35 | 0.20 |
| 3 | $10^{-7}$ | 0.55 | 0.31 |
| 4 | $5 \times 10^{-7}$ | 0.83 | 0.46 |
| 5 | $10^{-6}$ | 1.06 | 0.57 |
| 6 | $2 \times 10^{-6}$ | 1.33 | 0.75 |
| 7 | $3 \times 10^{-6}$ | 1.57 | 0.95 |
| 8 | $4 \times 10^{-6}$ | 1.75 | 1.02 |
| 9 | $5 \times 10^{-6}$ | 1.95 | 1.21 |
| 10 | $6 \times 10^{-6}$ | 2.08 | 1.38 |
| 11 | $7 \times 10^{-6}$ | 2.28 | 1.61 |
| 12 | $8 \times 10^{-6}$ | 2.4 | 1.78 |

Selective Sensing of L-Tyrosine and/or L-Cysteine

Example 34

Metal oxide modified MICP film based sensor gave selective response to L-tyrosine or L-cysteine in presence of equal amounts of other amino acids L-serine, L-valine, L-leucine and L-Phenylalanine and admixtures of L-tyrosine and L-cysteine in aqueous media using the determination procedures described in examples 31, 32 and 33 respectively. [FIG. 4]

Regeneration & Reusability of MICP Based Sensing Films

Example 35

The MICP film was prepared by electropolymerising 0.002, 0.003 and 0.004M of pyrrole in 20 ml of acetonitrile as supporting electrolyte containing 0.01M of tetrabutyl ammonium perchlorate and 35 μl of trifluoroacetic acid at a deposition potential 0.9V vs Ag/AgCl for a duration of 60 s in presence of $10^{-3}$M of L-tyrosine template onto glassy carbon electrode. The electrode was then taken out and template is then ejected out by electrochemical overoxidation in sodium hydroxide (>0.1M) by repeated cycling in the potential window of 0.8 to 1.2V vs Ag/AgCl for a minimum of 100 times at scan rate of 50 mV/s. The template leached MICP film electrode is then washed by cycling a minimum of 75 times in the potential window of 0 to 0.9V vs Ag/AgCl at scan rate of 100 mV/s. Subsequently, the above film electrode is stabilized in pH 5.5 phosphate buffer by cycling in the potential window of 0 to 0.9V for minimum of 20 times at 50 mV/s to obtain MICP film based electrode for L-tyrosine sensing. The sensing of L-tyrosine using the MICP modified GC electrode can be done by differential pulse voltammetric scanning in the potential window of 0 to 0.9V. The sensing surface is regenerated by stirring in pH 5.5 phosphate buffer over a period in the range of 1 to 5 min. for removal of oxidized tyrosine and can be reused for 25 to 35 times before coating a fresh MICP film.

Example 36

The L-cysteine and L-tyrosine & L-cysteine sensing MICP films prepared by processes described in examples 1 to 8 can be regenerated by stirring in pH 5.5 phosphate buffer for removal of oxidized tyrosine and/or cysteine and can be reused 30 times before coating a fresh MICP film.

Regeneration & Reusability of Metal Oxide Modified MICP Sensing Films

Example 37

The MICP film was prepared (as mentioned in Example 2) by electropolymerising 0.003M of pyrrole in 20 ml of acetonitrile as supporting electrolyte containing 0.01M of tetrabutyl ammonium perchlorate and 35 μl of trifluoroacetic acid at a deposition potential of 0.9V vs Ag/AgCl for a duration of 60 s in presence of $10^{-3}$ M of L-tyrosine and/or L-cysteine template onto glassy carbon electrode. The electrode was then taken out and template is then ejected out by electrochemical overoxidation in sodium hydroxide (>0.1M) by repeated cycling in the potential window of 0.8 to 1.2V vs Ag/AgCl for a minimum of 100 times at scan rate of 50 mV/s. The template leached MICP film electrode is then washed by cycling a minimum of 75 times in the potential window of 0 to 0.9V vs Ag/AgCl at scan rate of 100 mV/s. Subsequently, the above film electrode is stabilized in pH 5.5 phosphate buffer by cycling in the potential window of 0 to 0.9V for minimum of 20 times at 50 mV/s to obtain MICP film based electrode for L-tyrosine and/or L-cysteine sensing. Metal oxide modified MICP film was prepared by potentiostatic deposition of metals from $3 \times 10^{-5}$M of $Cu^{2+}$ or $Hg^{2+}$ or $Pd^{2+}$ or $Au^{3+}$ or $Pt^{4+}$ etc solutions for 5 s at −0.3V and then anodically scanning in the potential window of 0 to 0.9V to form corresponding metal oxide coatings for selective sensing of L-tyrosine and/or L-cysteine. Metal oxide islands formed on the electrode is removed and the molecularly imprinted polypyrrole surface is replenished for next cycle of quantification by holding the electrode over a potential in the range −0.15 to 0.075 V for a period in the range 7 to 10 seconds (in case of metal oxide modified MICP) followed by stirring in pH 5.5 phosphate buffer for a period of 1 to 5 min. (for all modified electrodes) for removal of oxidized amino acid. This process can be repeated at least 25 to 35 times without renewing the sensing substrate.

Example 38

The metal oxide modified MICP films prepared by the combination of processes explained in examples 10 to 30 can be regenerated and reused as described in example 37. Metal oxide islands formed on the electrode is removed and the molecularly imprinted polypyrrole surface is replenished for next cycle of quantification by holding the electrode at 0V~10 seconds (in case of metal oxide modified MICP) followed by stirring in pH 5.5 phosphate buffer (for all modified electrodes) for removal of oxidized amino acid. This process can be repeated at least 30 times without renewing the sensing substrate.

Method of Utilization of the Sensors

Example 39

All the modified electrodes can be used by the combination of the steps involving
i) process of preparation of MICPs as described in examples 1 to 8
ii) over-oxidation of MICP film as described in examples 1 to 8
iii) conditioning and stabilizing as described in examples 1 to 8 iv) process of preparing metal oxide coated MICP films (MO-MICPs) as described in examples 10 to 30
v) anodic scanning in the differential pulse mode in the potential window of 0-0.9V as described in examples 10 to 30
vi) determination of amino acids (L-tyrosine and/or L-cysteine as described in examples 31 to 33
vii) regeneration and reuse of sensing films based on the steps as elucidated in examples 35 to 38. The selectivity of the sensor in presence of various amino acids like serine, valine, phenylalanine, cysteine, leucine shows that the sensor exhibits more than 40 fold selectivity for tyrosine over the respective amino acids. The comparison of the present sensor with that of the existing electrodes mentioned in the background of the invention shows better selectivity.

ADVANTAGES OF THE PRESENT INVENTION

The major advantage of the present invention is significant selectivity for L-tyrosine and/or L-cysteine in presence of several other structurally similar amino acids compared to existing chemically/electrochemically modified sensors.

Another advantage accrued on modification with metal oxide (oxides of $Cu^{2+}$, $Hg^{2+}$, $Pd^{2+}$, $Au^{3+}$, $Pt^{4+}$ etc) is significant enhancement in sensitivity and lowering of the limit of detection during voltammetric sensing.

The all film coated sensors are compatible with aqueous media which is one of the major bottlenecks in biomolecule sensing using molecularly imprinted polymers.

There is ease of regeneration of MICP and metal oxide modified MICP films by holding the electrode at 0.0 V for 10 s and stirring in pH 5.5 phosphate buffer.

Various film coated GC electrodes are reusable for sequential or simultaneous differential pulse voltammetric sensing of L-tyrosine and/or L-cysteine.

We claim:

1. A process of preparing an amino acid sensor comprising a substrate coated with a polymer selected from molecularly imprinted conducting polymer (MICP) or metal oxide modified molecularly imprinted conducting polymer (MOMICP), comprising the steps of:
    (a) electropolymerizing pyrrole monomer in the presence of a template of amino acid selected from a group consisting of L-tyrosine, L-cysteine and a combination thereof to be imprinted in acetonitrile containing tetrabutyl ammonium perchlorate and trifluoacetic acid onto a substrate to obtain an MICP film based electrode;
    (b) leaching out the template from the electrode as obtained in step (a) by electrochemical over-oxidation followed by washing by cycling in phosphate buffer of pH 2 and subsequently stabilizing in phosphate buffer of pH 5.5 to obtain a template leached MICP, or a dual template leached MICP film coated electrode;
    (c) depositing metal selected from a group consisting of $Cu^{2+}$, $Hg^{2+}$, $Pd^{2+}$, $Au^{3+}$, and $Pt^{4+}$ on to the template leached and stabilized MICP or the dual template leached MICP electrode as obtained in step (b) followed by anodically scanning to obtain the respective MOMICP film coated electrode to be used as the amino acid sensor.

2. The process as claimed in claim 1 wherein a ratio of the pyrrole and the template is maintained between 400:1 to 2:1 within a concentration range of $2 \times 10^{-3}$ to $4 \times 10^{-3}$ M of the pyrrole and $10^{-5}$ to $10^{-3}$ M of the template.

3. The process as claimed in claim 1, wherein in step (a) a volume of the acetonitrile is 20 ml, a volume of the trifluoacetic acid is in a range of 0.5 to 35 µl and a concentration of the tetrabutyl ammonium perchlorate is in a range of 0.01 to 0.1M.

4. The process as claimed in claim 1, wherein in step (a) the electropolymerization is done at a deposition potential ranging from 0.8 to 0.9V vs Ag/AgCl for a period in a range of 55 to 65 seconds.

5. The process as claimed in claim 1, wherein in step (a) the substrate is a glassy carbon electrode (GCE) surface.

6. The process as claimed in claim 1, wherein in step (b) the electrochemical over-oxidation is done in the presence of 0.08-0.1M NaOH at a potential ranging between 0.8 to 1.2V vs Ag/AgCl for a minimum of 100 times at a scan rate of 40-70 mV/s.

7. The process as claimed in claim 1, wherein in step (b) the washing is done by cycling in the phosphate buffer for a minimum of 75 times in a potential ranging between 0 to 0.9V vs Ag/AgCl at a scan rate in a range of 75 to 125 mV/s.

8. The process as claimed in claim 1, wherein in step (b) stabilizing is done at a potential ranging between 0-0.9 V for a minimum of 20 times at a scan rate in the range of 50 to 70 mV/s.

9. The process as claimed in claim 1, wherein in step (c) the deposition of metal on the electrode obtained in step (b) is done by holding the electrode potentiostatically in a range of −0.28 to −0.32V for a period ranging between 4.5 to 5 seconds.

10. The process as claimed in claim 1, wherein in step (c) the anodic scanning is done at a potential in a range of 0 to 0.9V.

11. The process as claimed in claim 1, wherein the coated electrode of step (b) or (c) is reusable for 25 to 35 times by bringing back to starting potential in a range of −0.15 to 0.075 V and stirring in pH 5.5 phosphate buffer.

12. The process as claimed in claim 1, wherein the coated electrode of step (b) can be regenerated after use by stirring in pH 5.5 phosphate buffer for a period in a range of 1 to 5 min to remove oxidized tyrosine.

13. A calibration process comprising the steps of:
    dipping the coated electrode obtained in steps (b) or (c) of claim 1 into an electrochemical cell wherein the coated electrode is a working electrode; and
    providing a platinum foil counter electrode and Ag/AgCl reference electrode wherein the electrochemical cell contains a known amount of amino acid in a 0.075 to 0.15 M phosphate buffer solution;
wherein differential pulse voltammograms by scanning in a potential ranging between 0 to 0.9V at modulation amplitude in a range of 50 to 300 mV are recorded and a calibration graph is prepared by plotting current flowing between the working and the counter electrodes against the amino acid concentration.

14. The process as claimed in claim 1, wherein the coated electrode of step (c) can be regenerated after use by holding the electrode at a potential in a range of −0.15 to 0.075V for a period in a range of 7 to 10 seconds for metal oxide removal, followed by stirring in pH 5.5 phosphate buffer for a period in a range of 1 to 5 min to remove oxidized tyrosine.

* * * * *

UNITED STATES PATENT AND TRADEMARK OFFICE
CERTIFICATE OF CORRECTION

PATENT NO. : 9,239,311 B2  
APPLICATION NO. : 13/983229  
DATED : January 19, 2016  
INVENTOR(S) : Varghese et al.

Page 1 of 1

It is certified that error appears in the above-identified patent and that said Letters Patent is hereby corrected as shown below:

ON THE TITLE PAGE

Item (73) Assignee: Please delete "Council of Industrial & Scientific Research" and substitute therefor --Council of Scientific & Industrial Research--.

Signed and Sealed this  
Third Day of May, 2016

Michelle K. Lee  
*Director of the United States Patent and Trademark Office*